United States Patent
Cai et al.

(10) Patent No.: US 10,870,870 B2
(45) Date of Patent: Dec. 22, 2020

(54) ENGINEERING STRAIN AND APPLICATION THEREOF IN PRODUCTION OF DANSHENSU

(71) Applicant: Jiangnan University, Wuxi (CN)

(72) Inventors: Yujie Cai, Wuxi (CN); Tianzhen Xiong, Wuxi (CN); Jinbin Liu, Wuxi (CN); Yanrui Ding, Wuxi (CN); Yajun Bai, Wuxi (CN); Xiaohui Zheng, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 16/542,787

(22) Filed: Aug. 16, 2019

(65) Prior Publication Data

US 2019/0376100 A1 Dec. 12, 2019

Related U.S. Application Data

(63) Continuation of application No. PCT/CN2018/111895, filed on Oct. 25, 2018.

(30) Foreign Application Priority Data

| Apr. 19, 2018 | (CN) | 2018 1 0352649 |
| Apr. 19, 2018 | (CN) | 2018 1 0352693 |
| Apr. 19, 2018 | (CN) | 2018 1 0352695 |

(51) Int. Cl.

| C12P 13/06 | (2006.01) |
| C12N 9/00 | (2006.01) |
| C12N 9/10 | (2006.01) |
| C12P 7/42 | (2006.01) |
| C12N 9/04 | (2006.01) |

(52) U.S. Cl.
CPC ............ *C12P 13/06* (2013.01); *C12N 9/0006* (2013.01); *C12N 9/1096* (2013.01); *C12P 7/42* (2013.01); *C12Y 101/01027* (2013.01); *C12Y 104/01002* (2013.01)

(58) Field of Classification Search
None
See application file for complete search history.

(56) References Cited

FOREIGN PATENT DOCUMENTS

CN 103667371 A 3/2014

OTHER PUBLICATIONS

Prather et al., "De novo biosynthetic pathways: rational design of microbial chemical factories", Current Opinion in Biotechnology 2008, 19:468-474.*
Kizer et al., "Application of Functional Genomics to Pathway Optimization for Increased Isoprenoid Production", Applied and Environmental Microbiology, May 2008, vol. 74, No. 10, p. 3229-3241.*

* cited by examiner

*Primary Examiner* — Suzanne M Noakes
(74) *Attorney, Agent, or Firm* — IPro, PLLC

(57) ABSTRACT

The present disclosure discloses an engineering strain and application thereof in joint production of Danshensu and alanine, and belongs to the technical field of bioengineering. The present disclosure constructs a three-enzyme co-expression genetic engineering strain, and realizes joint production of Danshensu and alanine. Further, the transport of a substrate is promoted and decomposition of products is reduced by knocking out or enhancing expression of related genes on *E. coli* genome. The genetic engineering strain provided by the present disclosure can produce optically pure D-danshensu and L-danshensu, and jointly produce pyruvic acid. The production process is simple, raw materials are easily available, impurities are fewer, and a good industrial application prospect is achieved.

9 Claims, No Drawings
Specification includes a Sequence Listing.

ENGINEERING STRAIN AND APPLICATION THEREOF IN PRODUCTION OF DANSHENSU

TECHNICAL FIELD

The present disclosure relates to an engineering strain and application thereof in production of Danshensu, and belongs to the technical field of bioengineering.

BACKGROUND

Danshensu extracted from *Salvia miltiorrhiza*, has scientific names of R-(+)-3-(3,4-dihydroxyphenyl)-2-hydroxypropanoic acid and D-(+)-6-(3,4-dihydroxyphenyl) lactic acid, has English names of danshensu, D-DSS, R-DSS, (R)-(+)-3-(3,4-dihydroxyphenyl)-lactic acid, and (R)-(+)-3-(3,4-dihydroxyphenyl)-2-hydroxypropanoic acid, and is a dextrophenolic acid compound. Currently, there is no natural L-danshensu.

Danshensu is an important active ingredient in a water extract of *Salvia miltiorrhiza*, and the structure in the water extract of *Salvia miltiorrhiza* was obtained and identified in China in 1980 (Study on Water-soluble Active Ingredients of *Salvia miltiorrhiza*, Structure of II.D(+)β(3,4-Dihydroxyphenyl)Lactic Acid, Shanghai First Medical College Journal, 1980, 05(7), 384-385). Various studies have shown that Danshensu has important pharmacological effects and has unique effects in treatment of cardiovascular and cerebrovascular diseases.

At present, Danshensu is mainly extracted from *Salvia miltiorrhiza* (patent CN200810038853.9). The content of Danshensu in *Salvia miltiorrhiza* is low, the cost for planting *Salvia miltiorrhiza* is high, and the yield is limited. Therefore, Danshensu is not only expensive but also far from meeting the market demand. Patent CN201310559498.0 proposes a method for constructing *Escherichia coli* genetically engineered strain to produce Danshensu by glucose fermentation. Since the anabolic pathway involves the use of a hydroxylase, the enzyme is likely to oxidize a metabolic process product and affect the yield of Danshensu. At the same time, because *E. coli* fermentation is a high oxygen consumption process, it also oxidizes Danshensu. Therefore, the current method has lower yield, and the cost will be higher than that of a plant extraction process. Patent CN201210190171.6 proposes a method for producing Danshensu by hydrolyzing salvianolic acid B. Salvianolic acid B needs to be extracted from *Salvia miltiorrhiza*, and the chemical hydrolysis process has a large number of side reactions, which is also not suitable for large-scale production. A catalyst for chiral synthesis of Danshensu (patent CN201210420488.4) is extremely expensive and currently only stays at the laboratory level.

As early as 1988, Roth et al. proposed a method for treating levodopa by a chemical method to obtain the corresponding 3,4-dihydroxyphenylpyruvic acid, and then synthesizing S-(+)-3-(3,4-dihydroxyphenyl)-2-hydroxypropanoic acid (S-DSS, L-DSS) by an enzymatic method (Enzymatic Synthesis of (S)-(−)-3-(3,4-Dihydroxyphenyl)lactic Acid, Arch. Pharm. (Weinheim) 321, 179-180 (1988)). Z. Findrik, et al. used snake venom amino acid oxidase to convert levodopa into 3,4-dihydroxyphenylpyruvic acid, then used D-lactate dehydrogenase for reduction to produce D-(3,4-dihydroxyphenyl)lactic acid (Modelling and Optimization of the (R)-(+)-3,4-dihydroxyphenyllactic Acid Production Catalyzed with D-lactate dehydrogenase from *Lactobacillus leishmannii* Using Genetic Algorithm, Chem. Biochem. Eng. Q. 19 (4) 351-358 (2005)). Preparation of the 3,4-dihydroxyphenylpyruvic acid intermediate by the two methods is costly and complicated in operation.

SUMMARY

Based on the defects of various current methods, the present disclosure provides an optically pure Danshensu production method based on transaminase, and constructs a multi-enzyme co-expression engineering strain to achieve efficient production of Danshensu. The present disclosure provides a recombinant strain which can produce Danshensu at a low cost. At the same time, the present disclosure also provides the construction and application of the strain.

The present disclosure is firstly directed to a recombinant strain which can produce optically pure Danshensu at a low cost. The recombinant strain simultaneously expresses α-hydroxycarboxylate dehydrogenase and L-α-amino acid transaminase, and any one of the following: glucose dehydrogenase, L-lactate dehydrogenase, and L-glutamate dehydrogenase, and a gene related to decomposition of phenolic compounds is knocked out on the basis of a host *E. coli*.

In an example, the α-hydroxycarboxylate dehydrogenases are D-α-hydroxycarboxylate dehydrogenase, and are from *Lactobacillus plantarum* ATCC 14917, *Enterococcus faecalis* ATCC 35038 or *Lactobacillus fermentum* ATCC 14931.

In an example, the α-hydroxycarboxylate dehydrogenases are L-α-hydroxycarboxylate dehydrogenase, and are from *Bacillus coagulans* DSM 1, *Weissella confusa* strain DSM 20196, or *Lactobacillus fermentum* ATCC 14931.

In an example, the α-hydroxycarboxylate dehydrogenases are D-α-hydroxycarboxylate dehydrogenase, of which the amino acid sequences have an accession NO of WP_003643296.1, WP_002335374.1, or EEI22188.1 on NCBI; α-hydroxycarboxylate dehydrogenases are L-α-hydroxycarboxylate dehydrogenase, of which the amino acid sequences have accession NO of WP_013858488.1, WP_003607654.1 or WP_035430779.1 on NCBI.

In an example, the nucleotide sequences of D-α-hydroxycarboxylate dehydrogenase have accession NO. of NZ_GL379761 REGION: COMPLEMENT(533562 . . . 534560), NZ_KB944641 REGION: 161892 . . . 162830, or ACGI01000078 REGION: 20793 . . . 21791 on NCBI; the nucleotide sequences of L-α-hydroxycarboxylate dehydrogenase have accession NO. of NZ_ATUM01000014 REGION: 39316 . . . 40254, NZ_JOAY01000006 REGION: 69708 . . . 70640, or NZ_GG669901 REGION: 45517 . . . 46470 on NCBI.

In an example, the L-α-amino acid transaminases are from *E. coli* BL21, *Lactobacillus plantarum* ATCC 14917, or *Lactobacillus paracasei* ATCC 334.

In an example, the amino acid sequences of L-α-amino acid transaminase have accession NO of WP_000462687.1, WP_000486988.1, WP_003643296.1, or YP_806114.1 on NCBI.

In an example, the nucleotide sequences of L-α-amino acid transaminase have accession NO of NC_012892 REGION: COMPLEMENT (989603 . . . 990793), NC_012892 REGION: 4174517 . . . 4175710, NZ_GL379768 REGION: complement (121900 . . . 123087), or NC_008526 REGION: complement (840419 . . . 841594) on NCBI.

In an example, the glucose dehydrogenase is from *Bacillus subtilis* ATCC 13952.

In an example, the amino acid sequence of the glucose dehydrogenase has an accession NO of WP_013351020.1 on NCBI.

In an example, the nucleotide sequence of the glucose dehydrogenase has an accession NO of NZ_CP009748 REGION: 386154 . . . 38693 on NCBI.

In an example, the L-lactate dehydrogenase is from *Lactococcus lactic* ATCC 19257.

In an example, the amino acid sequence of the L-lactate dehydrogenase has an accession NO of WP_003131075.1 on NCBI.

In an example, the nucleotide sequence of the L-lactate dehydrogenase has an accession NO of NZ_JXJZ01000017 REGION: 18532 . . . 19509 on NCBI.

In an example, the L-glutamate dehydrogenases are from *E. coli* BL21, *Rhodobacter sphaeroides* ATCC BAA-808, *Clostridium symbiosum* ATCC 14940, or *Bacillus subtilis* 168.

In an example, the amino acid sequences of the L-glutamate dehydrogenase have accession NO of WP_000373021.1, WP_011338202.1, WP_003497202.1, or WP_010886557.1 on NCBI.

In an example, the nucleotide sequences of L-glutamate dehydrogenase have accession NO of NC_012892 REGION: 1786741 . . . 1788084, NC_007493 REGION: complement (2129131 . . . 2130558), NZ_KE992901 REGION: complement (17603 . . . 18955), or NC_000964 REGION: complement (2402067 . . . 2403350) on NCBI.

In an example, the recombinant strain is a recombinant engineering strain obtained by ligating genes encoding L-α-amino acid transaminase, α-hydroxycarboxylate dehydrogenase and any one of glucose dehydrogenase, L-lactate dehydrogenase and L-glutamate dehydrogenase to a plasmid to construct a three-gene co-expression recombinant plasmid, and then transforming the recombinant plasmid into a corresponding strain.

In an example, the recombinant strain is constructed by using *E. coli* BL21 (DE3) as a host.

In an example, the gene related to decomposition of the phenol compounds is any one or a combination of hpaD and mhpB.

In an example, the nucleotide sequences of the phenolic substance decomposing gene have accession NO of NC_012892 REGION: complement (4505585 . . . 4506436) and NC_012892 REGION: 339806 . . . 340750 on NCBI.

In an example, the recombinant strain further enhances expression of one or more of a pyruvic acid transporter gene, an L-lactic acid transporter gene, a glutamic acid transporter gene, an NAD synthesis gene, and a pyridoxal phosphate synthesis gene, where the pyruvic acid transporter genes, the L-lactic acid transporter gene and the glutamic acid transporter gene are not expressed at the same time.

In an example, enhanced expression is to add a constitutive promoter ahead of the gene to be enhanced in expression on an *E. coli* BL21 (DE3) genome.

In an example, the gene to be enhanced in expression is any one or more of the pyruvic acid transport-related genes, lldP (lactic acid transporter gene), gltS (glutamic acid transporter gene), nadA (NAD synthetic gene) and pdxJ (pyridoxal phosphate synthesis gene), where the pyruvic acid transport-related genes include btsT and ybdD (gene for transporting pyruvic acid into cells).

In an example, the accession NOs of btsT and ybdD on NCBI are: for nadA, NC_012892 REGION: 740487 . . . 741530; for pdxJ, NC_012892 REGION: complement (2567591 . . . 2568322).

In an example, the accession NO of the lldP on NCBI is: NC_012892 REGION: 3646638 . . . 3648293; for nadA, NC_012892 REGION: 740487 . . . 741530; for pdxJ, NC_012892 REGION: complement (2567591 . . . 2568322).

In an example, the accession NO of gltS on NCBI is: NC_012892 REGION: complement (3694931 . . . 3696136); for nadA, NC_012892 REGION: 740487 . . . 741530; for pdxJ, NC_012892 REGION: complement (2567591 . . . 2568322).

The present disclosure provides a method for producing Danshensu using the recombinant strain of the present disclosure.

In an example, the production of Danshensu is carried out by whole cell transformation.

In an example, in a whole cell transformation production system, cell wet weight is 1-200 g/L, and levodopa concentration is 1-200 g/L.

When the recombinant strain simultaneously expresses α-hydroxycarboxylate dehydrogenase, L-α-amino acid transaminase and glucose dehydrogenase, in the whole cell transformation production system, the pyruvic acid concentration is 1-200 g/L, and the glucose concentration is 1-200 g/L.

When the recombinant strain simultaneously expresses α-hydroxycarboxylate dehydrogenase, L-α-amino acid transaminase and L-lactate dehydrogenase, the whole cell transformation production system includes the L-lactic acid of 1-200 g/L.

When the recombinant strain simultaneously expresses α-hydroxycarboxylate dehydrogenase, L-α-amino acid transaminase and L-glutamate dehydrogenase, the whole cell transformation production system includes L-glutamic acid of 1-200 g/L.

The whole cell transformation production system has a pH of 6.0-9.0, and reacts at 15-40° C. for 1-48 hours.

The present disclosure constructs a novel multi-enzyme co-expression genetic engineering strain, and realizes low-cost production of Danshensu. Further, transport of a substrate is promoted and decomposition of products is reduced by knocking out or enhancing expression of related genes on the *E. coli* genome. The (D/L)-α-hydroxycarboxylate dehydrogenase selected by the present disclosure has the characteristics of poor substrate specificity and strong optical specificity, and can produce optically pure D-danshensu and L-danshensu. The production process is simple, raw materials are easily available, and a good industrial application prospect is achieved.

DETAILED DESCRIPTION

The functional core of the engineering strain provided by the present disclosure is that three enzymes, respectively L-α-amino acid transaminase, α-hydroxycarboxylate dehydrogenase, and any one of glucose dehydrogenase, L-lactate dehydrogenase and L-glutamate dehydrogenase, can be simultaneously expressed. The principle is: in the whole cell of the engineering strain, glucose dehydrogenase or L-lactate dehydrogenase or L-glutamate dehydrogenase uses NAD in the cell as a coenzyme to dehydrogenate the corresponding glucose, or L-lactate dehydrogenase or L-glutamate dehydrogenase generates NADH and corresponding gluconic acid or pyruvic acid or α-ketoglutaric acid; levodopa is deaminated by L-α-amino acid transaminase to generate 3,4-dihydroxyphenylpyruvic acid, and pyruvic acid is converted into alanine by ammonia; α-hydroxycarboxylate dehydrogenase uses NADH produced by the dehydrogenation process of glucose to reduce the 3,4-dihydroxyphenylpyruvic acid into Danshensu and simultaneously regenerate the coenzyme NAD. Further, transport of a substrate is promoted and decomposition of products is reduced by knocking out or enhancing expression of related genes on an *E. coli* genome.

1. Strains and Plasmids of the Present Disclosure

*Lactobacillus plantarum* ATCC 14917, *Enterococcus faecalis* ATCC 35038, *Lactobacillus fermentum* ATCC 14931, *Lactobacillus paracasei* ATCC 334, *Bacillus subtilis* ATCC 13952, *E. coli* BL21 (DE3) and *Lactococcus lactic* ATCC 19257 purchased from American Type Culture Collection (ATCC). *Bacillus coagulans* DSM 1 and *Weissella confusa* strain DSM 20196 purchased from Deutsche Sammlung von Mikroorganismen and Zellkulturen (DSMZ). PETDuet-1, pACYCDue-1, pCOLADuet-1 and pRSFDuet-1 plasmids and *E. coli* BL21(DE3) purchased from Novagen.

2. Knockout and Constitutive Enhanced Expression of Related Genes in *E. coli*

(1) Knockout of Genes Related to Decomposition of Phenolic Compounds in *E. coli* Phenolic Compound Phenolic substances in the present disclosure are highly susceptible to decomposition by enzymes in *E. coli*. According to the literature (Biodegradation of Aromatic Compounds by *E. coli*, Microbiol Mol Biol Rev. 2001, 65(4): 523-569.), related genes are knocked out to avoid decomposition of products and substrates. The selected genes are hpaD and mhpB, of which the accession NOs on NCBI are NC_012892 REGION: complement (4505585 . . . 4506436) and NC_012892 REGION: 339806 . . . 340750.

(2) Constitutive Enhanced Expression of *E. coli* Pyruvic Acid Transporter Gene

In the process of whole cell transformation, the substrate needs to be transported into the cell to carry out reaction. Enhancing pyruvic acid transport protein is helpful to rapid and long-term maintenance of high concentration of the intracellular substrate, and is favorable for the progress of the reaction. The selected pyruvic acid transport-related genes are btsT and ybdD, of which the accession NOs on NCBI are NC_012892 REGION: complement (4496239 . . . 4498389) and NC_012892 REGION: 592652 . . . 592849. Dopa is similar to aromatic amino acids, and needs to absorb amino acids and the like during cell culture. Therefore, the cells themselves express a large amount of amino acid transport protein, and need not to enhance expression.

(3) Constitutive Enhanced Expression of Important Genes Related to *E. coli* Coenzyme Synthesis In the reduction process of α-hydroxycarboxylate dehydrogenase, NADH needs to be used as a coenzyme. Enhanced expression of key enzymes in an *E. coli* NAD synthesis pathway can increase the level of NAD in the cells, thereby being beneficial to the production of Danshensu. The selected gene is nadA. The accession NO on NCBI is: NC_012892 REGION: 740487 . . . 741530.

Pyridoxal phosphate (amine) is a coenzyme of L-α-amino acid transaminase, and overexpression of the core gene pdxJ in the coenzyme pathway is beneficial to the synthesis of levodopa. The accession NO on NCBI is: NC_012892 REGION: complement (2567591 . . . 2568322).

3. Enzyme Selection (1) Selection of L-α-Amino Acid Transaminase

L-α-amino acid transaminase is widely present in bacteria, fungi and mammalian cells. Usually a transaminase with α-ketoglutaric acid or oxaloacetic acid as an ammonia receptor is most active. In this process, the α-ketoglutaric acid or oxaloacetic acid is expensive, while the value of the correspondingly produced glutamic acid or aspartic acid is much lower than that of the corresponding precursor. A comprehensive examination of the corresponding α-keto acids of 20 natural L-amino acids reveals that the prices of pyruvic acid and alanine are comparable. Therefore, the present disclosure selects the pyruvic acid as the ammonia receptor to realize joint production of alanine and Danshensu. The L-α-amino acid transaminase genes lpt and lct are cloned from *Lactobacillus plantarum* ATCC 14917 and *Lactobacillus paracasei* ATCC 334 respectively, and the amino acid sequences thereof have accession NOs of WP_003643296.1 and YP_806114.1 on NCBI. Two L-α-amino acid transaminase genes ect1 and ect2 are cloned from *E. coli* BL1 (DE3), and the amino acid sequences thereof have accession NOs of WP_000462687.1 and WP_000486988.1 on NCBI.

(2) Selection of α-Hydroxycarboxylate Dehydrogenase

According to the optimum substrate, α-hydroxycarboxylate dehydrogenase contains lactate dehydrogenase, aα-hydroxy acid isohexanoate dehydrogenase, mandelic acid dehydrogenase, glyoxylate reductase, etc. These enzymes can act extensively on a variety of substrates to generate α-hydroxycarboxylic acids, usually named according to their substrates of optimum function. The present disclosure selects enzymes which are high in optical property and has a strong activity against 3,4-dihydroxyphenylpyruvic acid, to produce D- or L-danshensu. D-α-hydroxycarboxylate dehydrogenase genes lpldhd, efmdhd and lfldhd are respectively cloned from *Lactobacillus plantarum* ATCC 14917, *Enterococcus faecalis* ATCC 35038 and *Lactobacillus fermentum* ATCC 14931, and the amino acid sequences thereof have the accession NOs of WP_003643296.1, WP_002335374.1 and EEI22188.1 on NCBI. L-α-hydroxycarboxylate dehydrogenase genes bcldhl, wcldhl and lfldhl are respectively obtained from *Bacillus coagulans* DSM 1, *Weissella confusa* strain DSM 20196 and *Lactobacillus fermentum* ATCC 14931, and the amino acid sequences thereof have the accession NOs of WP_013858488.1, WP_003607654.1 and WP_035430779.1 on NCBI.

(3) Selection of Glucose Dehydrogenase

In biotransformation reactions, α-hydroxycarboxylate dehydrogenase requires NADH and/or NADPH as coenzyme, usually formate dehydrogenase, glucose dehydrogenase, phosphite dehydrogenase, etc. Glucose dehydrogenase is the most active compared to other enzymes, and thus the present disclosure obtains the glucose dehydrogenase gene bsgdh (of which the amino acid sequence is WP_013351020.1) from *Bacillus subtilis* ATCC 13952.

(4) Selection of L-Lactate Dehydrogenase

L-lactic acid is the most inexpensive organic acid, and alanine produced by transamination of pyruvic acid after dehydrogenation has a high added value. L-lactate dehydrogenase is widely present in a variety of microorganisms. Using L-lactic acid as a substrate, hydrogen generated on L-lactic acid is transferred to the coenzyme NAD or NADP to produce NADH or NADPH. NADH or NADPH can be used as a hydrogen donor of the aforementioned α-hydroxylcarboxylic acid dehydrogenase. Generally, lactate dehydrogenase with NADH (NADPH) as a coenzyme tends to synthesize lactic acid with pyruvic acid as a substrate. However, when the lactic acid is excessive, and the like, the lactate dehydrogenase will remove the hydrogen of the lactic acid to produce pyruvic acid. The present disclosure obtains the L-lactate dehydrogenase gene llldh (of which the amino acid sequence is WP_003131075.1) from *Lactococcus lactic* ATCC 19257.

(5) Selection of L-Glutamate Dehydrogenase

L-glutamic acid is the most inexpensive amino acid, and α-ketoglutaric acid produced after dehydrogenation can be used as an ammonia receptor for levodopa transamination and deamination. L-glutamate dehydrogenase is widely found in almost all organisms. Using L-glutamic acid as a substrate, hydrogen produced on L-glutamic acid is transferred to the coenzyme NAD or NADP to produce NADH or NADPH. NADH or NADPH can be used as a hydrogen donor of the aforementioned hydroxylcarboxylic acid dehydrogenase. The present disclosure obtains L-glutamic acid genes ecgdh (of which the amino acid sequence is WP_000373021.1), rsgdh (of which the amino acid sequence is WP_011338202.1), csgdh (of which the amino acid sequence is WP_003497202.1) and bsgdh (of which the amino acid sequence is WP_010886557.1) from *E. coli* BL21, *Rhodobacter sphaeroides* ATCC BAA-808, *Clostridium symbiosum* ATCC 14940 and *Bacillus subtilis* 168, respectively.

4. Construction of Three-Enzyme Co-Expression System and Cell Culture

At present, there are many methods for *E. coli* multi-gene co-expression (*E. coli* Multi-gene Co-expression Strategy, China Biotechnology, 2012, 32(4): 117-122). The present disclosure adopts a method described by Liu Xianglei (Production of Shikimic Acid and Resveratrol by Transformation of *E. coli* by Synthetic Biotechnology, 2016, Shanghai Pharmaceutical Industry Research Institute, Ph.D. Thesis). Each gene contains a T7 promoter and an RBS binding site at the front, and each gene has a T7 terminator at the back. Theoretically, because each gene has T7 and RBS at the front, the expression intensity of the gene is less affected by the order. Each plasmid contains three genes (genes corresponding to L-α-amino acid transaminase, (D/L)-α-hydroxycarboxylate dehydrogenase, and glucose dehydrogenase or L-lactate dehydrogenase or L-glutamate dehydrogenase). The constructed plasmid is heat-transferred into *E. coli* competent cells, and the *E. coli* competent cells are coated on an antibiotic solid plate. Positive transformants are obtained by screening, that is, recombinant *E. coli* is obtained. Cells are cultured according to a classical recombinant *E. coli* culture and induction expression program. Recombinant *E. coli* is transferred to an LB fermentation medium (containing peptone of 10 g/L, yeast powder of 5 g/L, and NaCl of 10 g/L) at a volume ratio of 2%.

After the cell OD600 reaches 0.6-0.8, IPTG with a final concentration of 0.4 mM is added, and induction expression and culture are carried out at 20° C. for 8 h. After induction expression is completed, the cells are collected by centrifugation at 20° C. and 8000 rpm for 20 minutes.

5. Whole Cell Transformation Production of Pure Danshensu

In a cell transformation production system, cell wet weight is 1-200 g/L, and levodopa concentration is 1-200 g/L.

When the recombinant strain simultaneously expresses α-hydroxycarboxylate dehydrogenase, L-α-amino acid transaminase and glucose dehydrogenase, in the whole cell transformation production system, the pyruvic acid concentration is 1-200 g/L, and the glucose concentration is 1-200 g/L.

When the recombinant strain simultaneously expresses α-hydroxycarboxylate dehydrogenase, L-α-amino acid transaminase and L-lactate dehydrogenase, the whole cell transformation production system further includes L-lactic acid of 1-200 g/L.

When the recombinant strain simultaneously expresses α-hydroxycarboxylate dehydrogenase, L-α-amino acid transaminase and L-glutamate dehydrogenase, the whole cell transformation production system further includes L-glutamic acid of 1-200 g/L.

The whole cell transformation produces system has a pH of 6.0-9.0, and reacts at 15-40° C. for 1-48 hours.

After the end of transformation, the yield and configuration of Danshensu are determined by liquid chromatography. Levodopa has a low solubility and is a suspension containing an insoluble matter at high concentrations.

6. Detection and Analysis of Samples

Quantitative analysis of Danshensu: The transformed broth is detected and analyzed by a PerkinElmer Series 200 high performance liquid chromatograph with a differential refractive index detector. The chromatographic conditions are as follows: the mobile phase is methanol-0.1% formic acid water (40:60), a Hanbon Megres C18 chromatographic column (4.6×250 mm, 5 μm) is used, the flow rate is 1 ml/min, the column temperature is 30° C., and the injection volume is 20 μl.

Chiral analysis: A PerkinElmer Series 200 high performance liquid chromatograph with a UV detector is used for detection and analysis, a Chiralcel OD-H chiral column (4.6×250 mm) is used, the mobile phase volume ratio of n-hexane to isopropanol to trifluoroacetic acid is 80:20:0.1, the flow rate is 0.5 mL/min, the column temperature is 25° C., the injection volume is 20 μl, and the detection wavelength is 280 nm.

Danshensu has a relatively low solubility, and if crystallization appears in the transformation process, measurement is carried out after dilution.

The optical purity of Danshensu is evaluated by an enantiomeric excess value (% e.e).

When R-danshen is produced, the enantiomeric excess value % e.e=[(SR−SS)/(SR+SS)×100%]

When S-danshen is produced, the enantiomeric excess value % e.e=[(SS−SR)/(SR+SS)×100%]

where SS is the peak area of S-danshensu in the transformed broth, and SR is the liquid chromatography peak area of R-danshen in the transformed broth.

Example 1

By a method according to the literature Large scale validation of an efficient CRISPR/Cas-based multi gene editing protocol in *E. coli*. Microbial Cell Factories, 2017, 16(1):68, HpaD and mhpB on *E. coli* BL21(DE3) are singly or doubly knocked out. The gene knockout plasmids used in the present disclosure are pCasRed and pCRISPR-gDNA (hpaD sgRNA) which are introduced into *E. coli* BL21 (DE3) together with a homologous arm (hpaD donor). Cas9/sgRNA induces double-strand break in the hpaD gene locus of the host, the recombinase Red integrates the hpaD donor onto the hpaD gene to realize knockout of the gene, and the gene is verified by sequencing. hpaD sgRNA, hpaD donor, mhpB sgRNA and mhpB donor respectively as shown in SEQ ID NO:9, SEQ ID NO:10, SEQ ID NO:11 and SEQ ID NO:12. MhpB is knocked out in the same way.

A solution having a pH of 7 is prepared with the levodopa or D-danshensu of 4 g/L, the amount of wet cells is 200 g/L, and the concentration is measured after the solution is placed at 35° C. for 10 hours. The residual amounts of levodopa and D-danshensu in the reaction system are shown in Table 1.

TABLE 1

Residual concentrations of substrates and
products decomposed by different strains

|  | Levodopa g/L | D-danshensu g/L |
|---|---|---|
| E. coli BL21 (DE3) | 1.6 | 1.4 |
| E. coli BL21 (ΔhpaDΔmhpB, DE3) | 3.7 | 3.5 |
| E. coli BL21 (ΔhpaD, DE3) | 2.0 | 2.8 |
| E. coli BL21 (ΔmhpB, DE3) | 1.7 | 1.5 |

Obviously, E. coli BL21 (AhpaDAmhpB, DE3) has the best effect and is named E. coli HM.

Example 2

During screening of L-α-amino acid transaminase, a variety of L-α-amino acid transaminase genes are cloned from E. coli and lactobacilli respectively and expressed in E. coli BL21(DE3). The crude enzyme activity is determined by cell disruption, and the activities of various enzymes are compared with pyruvic acid as a receptor. The activity of L-α-amino acid transaminase is determined according to the literature (Transaminase-catalyzed asymmetric synthesis of aromatic L-amino acids. Chinese Journal of Biotechnology, 2012, 28(11): 1346-1358.). The results are shown in Table 2. Therefore, it is preferred to select L-α-amino acid transaminase ect1 derived from E. coli for transamination and deamination of levodopa.

The activities of various enzymes with α-ketoglutaric acid as a receptor are compared. The activity of L-α-amino acid transaminase is determined according to the method described in the literature (Transaminase-catalyzed asymmetric synthesis of aromatic L-amino acids. Chinese Journal of Biotechnology, 2012, 28(11): 1346-1358.). The results are shown in Table 3. Therefore, it is preferred to select L-α-amino acid transaminase lct derived from Lactobacillus paracasei ATCC 334 for transamination and deamination of levodopa.

The induction expression method is: recombinant E. coli is transferred to an LB fermentation medium (containing peptone of 10 g/L, yeast powder of 5 g/L and NaCl of 10 g/L) at a volume ratio of 2%. After the cell OD600 reaches 0.6-0.8, IPTG with a final concentration of 0.4 mM is added, and induction expression and culture are carried out at 20° C. for 8 h. After induction expression is completed, the cells are collected by centrifugation at 20° C. and 8000 rpm for 20 minutes.

TABLE 2

Comparison of activity of different
L-α-amino acid transaminases

| Recombinant strain | Activity U/ml |
|---|---|
| E. coli BL21 (DE3)/pETDuet-1-ect1 | 2 |
| E. coli BL21 (DE3)/pETDuet-1-ect2 | 0.01 |
| E. coli BL21 (DE3)/pETDuet-1-lpt | 1.2 |
| E. coli BL21 (DE3)/pETDuet-1-lct | 0.6 |

TABLE 3

Comparison of activity of different
L-α-amino acid transaminases

| Recombinant strain | Activity U/ml |
|---|---|
| E. coli BL21/pETDuet-1-ect1 | 2.1 |
| E. coli BL21/pETDuet-1-ect2 | 0.9 |
| E. coli BL21/pETDuet-1-lpt | 2.4 |
| E. coli BL21/pETDuet-1-lct | 3.1 |

Example 3

The enzymatic properties of α-hydroxycarboxylate dehydrogenase are compared. Usually, this enzyme may also have the ability to reduce pyruvic acid to produce lactic acid, so that an enzyme that cannot reduce or very weakly reduces pyruvic acid is preferred. Using pyruvic acid as a substrate, the reducing ability of different enzymes is compared. By a method according to the literature (Study on cloning expression, purification and enzymatic property of Serratia marcescens H3010 fermented D-lactate dehydrogenase gene. Industrial Microbiology, 2012, 42(04):30-37.), the activity of NAD as a coenzyme to reduce pyruvic acid is determined, and the experimental results are shown in Table 4.

TABLE 4

Comparison of activity of various α-hydroxycarboxylate
dehydrogenases in reduction of pyruvic acid

| Recombinant strain | Activity U/ml |
|---|---|
| E. coli HM/pETDuet-1-lpldhd | 6.6 |
| E. coli HM/pETDuet-1-efmdhd | 0 |
| E. coli HM/pETDuet-1-lfldhd | 0.7 |
| E. coli HM/pETDuet-1-bcldhl | 5.2 |
| E. coli HM/pETDuet-1-wcldhl | 0.2 |
| E. coli HM/pETDuet-1-lfldhl | 6.3 |

Example 4

The recombinant E. coli simultaneously expressing α-hydroxycarboxylate dehydrogenase, L-α-amino acid transaminase and glucose dehydrogenase is constructed: firstly, genes encoding L-α-amino acid transaminase, α-hydroxycarboxylate dehydrogenase and glucose dehydrogenase are ligated to a plasmid to obtain a three-gene co-expression recombinant plasmid. The plasmid is transformed into E. coli HM, and positive transformants are obtained by screening with an antibiotic plate to obtain recombinant E. coli.

After induction expression of the recombinant E. coli is completed, cells are collected, and in a reaction volume of 100 ml with cell wet weight of 40 g/L, levodopa of 40 g/L, pyruvic acid of 30 g/L, glucose of 30 g/L and pH of 8.0, reaction is carried out at 35° C. for 12 hours. After the end of transformation, the yield and configuration of Danshensu are determined by liquid chromatography, and the results are shown in Table 5.

TABLE 5

Comparison of various recombinant strains

| Recombinant strain | Danshensu Concentration g/L | Configuration | e.e % | Alanine g/L |
|---|---|---|---|---|
| E. coli HM/pETDuet-1-wcldhl-ect1-bsgdh | 18.3 | S | >99.9 | 9.3 |
| E. coli HM/pETDuet-1-bcldhl-ect1-bsgdh | 18.1 | S | >99.9 | 10.0 |
| E. coli HM/pETDuet-1-lfldhl-ect1-bsgdh | 17.9 | S | >99.9 | 9.6 |
| E. coli HM/pETDuet-1-efmdhd-ect1-bsgdh | 20.6 | R | >99.9 | 10.7 |
| E. coli HM/pETDuet-1-lpldhd-ect1-1-bsgdh | 15.8 | R | >99.9 | 9.8 |
| E. coli HM/pETDuet-1-lfldhd-ect1-bsgdh | 22.6 | R | >99.9 | 11.6 |

Example 5

The recombinant E. coli simultaneously expressing α-hydroxycarboxylate dehydrogenase, L-α-amino acid transaminase and L-lactate dehydrogenase is constructed: firstly, genes encoding the L-lactate dehydrogenase, L-α-amino acid transaminase and α-hydroxycarboxylate dehydrogenase are ligated to a plasmid to obtain a three-gene co-expression recombinant plasmid. The plasmid is transformed into E. coli HM, and positive transformants are obtained by screening with an antibiotic plate to obtain recombinant E. coli.

After induction expression of the recombinant E. coli is completed, cells are collected, and in a reaction volume of 100 ml with cell wet weight of 40 g/L, levodopa concentration of 40 g/L, pyruvic acid concentration of 30 g/L, and pH of 8.0, reaction is carried out at 35° C. for 12 hours. After the end of transformation, the yield and configuration of Danshensu are determined by liquid chromatography, and the results are shown in Table 6.

TABLE 6

Comparison of various recombinant strains

| Recombinant strain | Danshensu Concentration g/L | Configuration | e.e % | Alanine g/L |
|---|---|---|---|---|
| E. coli HM/pETDuet-1-wcldhl-ect1-llldh | 16.3 | S | >99.9 | 9.7 |
| E. coli HM/pETDuet-1-bcldhl-ect1-llldh | 5.7 | S | >99.9 | 4.6 |
| E. coli HM/pETDuet-1-lfldhl-ect1-llldh | 6.3 | S | >99.9 | 4.0 |
| E. coli HM/pETDuet-1-efmdhd-ect1-llldh | 17.1 | R | >99.9 | 8.6 |
| E. coli HM/pETDuet-1-lpldhd-ect1-1-llldh | 8.9 | R | >99.9 | 5.4 |
| E. coli HM/pETDuet-1-lfldhd-ect1-llldh | 15.5 | R | >99.9 | 8.4 |

Example 6

The recombinant E. coli simultaneously expressing α-hydroxycarboxylate dehydrogenase, L-α-amino acid transaminase and L-glutamate dehydrogenase is constructed: firstly, genes encoding the L-α-amino acid transaminase, α-hydroxycarboxylate dehydrogenase and L-glutamate dehydrogenase are ligated to a plasmid to obtain a three-gene co-expression recombinant plasmid. The plasmid is transformed into E. coli HM, and positive transformants are obtained by screening with an antibiotic plate to obtain recombinant E. coli.

After induction expression of the recombinant E. coli is completed, cells are collected, and in a reaction volume of 100 ml with cell wet weight of 40 g/L, levodopa concentration of 40 g/L, L-glutamic acid concentration of 30 g/L, and pH of 8.0, reaction is carried out at 35° C. for 12 hours. After the end of transformation, the yield and configuration of Danshensu are determined by liquid chromatography, and the results are shown in Table 7.

TABLE 7

Comparison of various recombinant strains

| Recombinant strain | Danshensu Concentration g/L | Configuration | e.e % |
|---|---|---|---|
| E. coli HM/pETDuet-1-wcldhl-bsgdh-lct | 19.6 | S | >99.9 |
| E. coli HM/pETDuet-1-bcldhl-bsgdh-lct | 19.4 | S | >99.9 |
| E. coli HM/pETDuet-1-lfldhl-bsgdh-lct | 14.5 | S | >99.9 |
| E. coli HM/pETDuet-1-efmdhd-bsgdh-lct | 21.7 | R | >99.9 |
| E. coli HM/pETDuet-1-lpldhd-bsgdh-1-lct | 17.1 | R | >99.9 |
| E. coli HM/pETDuet-1-lfldhd-bsgdh-lct | 22.5 | R | >99.9 |
| E. coli HM/pETDuet-1-efmdhd-bsgdh-ect1 | 14.3 | R | >99.9 |
| E. coli HM/pETDuet-1-efmdhd-bsgdh-ect2 | 21.4 | R | >99.9 |
| E. coli HM/pETDuet-1-efmdhd-bsgdh-lpt | 19.6 | R | >99.9 |
| E. coli HM/pCOLADuet-1-lfldhd-bsgdh-lct | 26.3 | R | >99.9 |
| E. coli HM/pRSFDuet-1-lfldhd-bsgdh-lct | 23.4 | R | >99.9 |
| E. coli HM/pCOLADuet-1-wcldhl-bsgdh-lct | 25.9 | S | >99.9 |

Example 7

By the method described in the literature Large scale validation of an efficient CRISPR/Cas-based multi gene editing protocol in E. coli. Microbial Cell Factories, 2017, 16(1):68, a medium expression intensity constitutive promoter (PG) ahead of the E. coli glyceraldehyde-3-phosphate dehydrogenase gene (gpdA) is added ahead of the corresponding gene on the E. coli HM genome, and the sequence is as shown in SEQ ID NO: 8.

When expression of the gene btsT is enhanced, the E. coli HM genome is used as a template, btsT-FF/btsT-FR, btsT-gpdA-F/btsT-gpdA-R and btsT-RF/btsT-RR are used as primers, upstream sequences, promoters and downstream sequences are amplified, and btsT-FF and btsT-RR are used as primers to fuse an expression cassette containing the gpdA promoter. Then, after the expression cassette is transferred into E. coli HM together with plasmids pCasRed and pCRISPR-gDNA (containing btsT sgRNA), Cas9/sgRNA induces double-strand break at the btsT gene locus of the host, the recombinase Red integrates the gpdA promoter ahead of the btsT gene, and the gene is verified by sequencing.

When expression of the gene ybdD is enhanced, the E. coli HM genome is used as a template, ybdD-FF/ybdD-FR, ybdD-gpdA-F/ybdD-gpdA-R and ybdD-RF/ybdD-RR are used as primers, upstream sequences, promoters and downstream sequences are amplified, and ybdD-FF and ybdD-RR are used as primers to fuse an expression cassette containing the gpdA promoter. Then, after the expression cassette is transferred into E. coli HM together with plasmids pCasRed and pCRISPR-gDNA (containing ybdD sgRNA), Cas9/sgRNA induces double-strand break at the ybdD gene locus of the host, the recombinase Red integrates the gpdA promoter ahead of the ybdD gene, and the gene is verified by sequencing.

Table 8 below shows the corresponding indexes of the primer name and the sequence identity number.

TABLE 8

Primer name and sequence identity number

| Name | Sequence identity number |
|---|---|
| btsT sgRNA | SEQ ID NO: 20 |
| btsT-FF | SEQ ID NO: 22 |
| btsT-FR | SEQ ID NO: 23 |
| btsT-gpdA-F | SEQ ID NO: 24 |
| btsT-gpdA-R | SEQ ID NO: 25 |
| btsT-RF | SEQ ID NO :26 |
| btsT-RR | SEQ ID NO: 27 |
| ybdD sgRNA | SEQ ID NO: 21 |
| ybdD-FF | SEQ ID NO: 28 |
| ybdD-FR | SEQ ID NO: 29 |
| ybdD-gpdA-F | SEQ ID NO: 30 |
| ybdD-gpdA-R | SEQ ID NO: 31 |
| ybdD-RF | SEQ ID NO: 32 |
| ybdD-RR | SEQ ID NO: 33 |

According to the induction expression method described in Example 2, various types of cells are collected for transformation analysis, and the results are shown in Table 9. In the whole cell transformation system with wet cell weight of 5 g/L, pyruvic acid of 50 g/L, levodopa of 20 g/L, glucose of 50 g/L, pH of 8.0, temperature of 40° C., and shaker speed of 250 rpm, the transformation time is 12 hours.

The *E. coli* HM (PG-btsT, PG-ybdD) with the best effect is named *E. coli* HMBY.

When expression of the gene lldP is enhanced, the *E. coli* HM genome is used as a template, upstream sequences, promoters and downstream sequences are amplified, and an expression cassette containing the gpdA promoter is obtained. Then, after the expression cassette is transferred into *E. coli* HM together with plasmids pCasRed and pCRISPR-gDNA (containing lldP sgRNA), Cas9/sgRNA induces double-strand break at the lldP gene locus of the host, the recombinase Red integrates the gpdA promoter ahead of the lldP gene, and the gene is verified by sequencing.

According to the induction expression method described in Example 2, various types of cells are collected for transformation analysis, and the results are shown in Table 10. In the whole cell transformation system with wet cell weight of 5 g/L, L-lactic acid of 50 g/L, levodopa of 20 g/L, pH of 8.0, temperature of 40 C, and shaker speed of 250 rpm, the transformation time is 12 hours.

TABLE 9

Comparison of transformation results

| | Danshensu | | | Alanine |
|---|---|---|---|---|
| Recombinant strain | Concentration g/L | Configuration | e.e % | g/L |
| *E. coli* HM (PG-btsT)/pCOLADuet-1-lfldhd-ect1-bsgdh | 4.3 | R | >99.9 | 2.7 |
| *E. coli* HM (PG-ybdD)/pCOLADuet-wcldhl-ect1-bsgdh | 4.6 | S | >99.9 | 3.1 |
| *E. coli* HM (PG-btsT)/pCOLADuet-1-lfldhd-ect1-bsgdh | 4.1 | R | >99.9 | 3.2 |
| *E. coli* HM (PG-ybdD)/pCOLADuet-1-wcldhl-ect1-bsgdh | 4.3 | S | >99.9 | 2.9 |
| *E. coli* HM (PG-btsT, PG-ybdD)/pCOLADuet-1-lfldhd-ect1-bsgdh | 5.8 | R | >99.9 | 4.1 |
| *E. coli* HM (PG-btsT, PG-ybdD)/pCOLADuet-1-wcldhl-ect1-bsgdh | 5.1 | R | >99.9 | 3.9 |
| *E. coli* HM/pCOLADuet-1-lfldhd-ect1-bsgdh | 4.5 | S | >99.9 | 2.9 |
| *E. coli* HM/pCOLADuet-1-wcldhl-ect1-bsgdh | 3.9 | R | >99.9 | 2.6 |

TABLE 10

Comparison of transformation results

| | Danshensu | | | Alanine |
|---|---|---|---|---|
| Recombinant strain | Concentration g/L | Configuration | e.e % | g/L |
| *E. coli* HM (PG-lldP)/pCOLADuet-1-lfldhd-ect1-llldh | 5.3 | R | >99.9 | 3.3 |
| *E. coli* HM (PG-lldP)/pCOLADuet-1-wcldhl-ect1-llldh | 7.0 | S | >99.9 | 3.8 |
| *E. coli* HM/pCOLADuet-1-lfldhd-ect1-llldh | 3.8 | R | >99.9 | 2.6 |
| *E. coli* HM/pCOLADuet-1-wcldhl-ect1-llldh | 5.5 | S | >99.9 | 3.7 |

E. coli HM/pCOLADuet-1-wcldhl-ect1-llldh 5.5 S>99.9 3.7

The E. coli HM (PG-lldP) with the best effect is named E. coli HML.

When expression of the gene gltS is enhanced, the E. coli HM genome is used as a template, upstream sequences, promoters and downstream sequences are amplified, and an expression cassette containing the gpdA promoter is obtained. Then, after the expression cassette is transferred into E. coli HM together with plasmids pCasRed and pCRISPR-gDNA (containing gltS sgRNA), Cas9/sgRNA induces double-strand break at the gltS gene locus of the host, the recombinase Red integrates the gpdA promoter ahead of the gltS gene, and the gene is verified by sequencing.

According to the induction expression method described in Example 2, various types of cells are collected for transformation analysis, and the results are shown in Table 11. In the whole cell transformation system with wet cell weight of 5 g/L, L-glutamic acid of 1 g/L, levodopa of 20 g/L, pH of 8.0, temperature of 40° C., and shaker speed of 250 rpm, the transformation time is 12 hours.

TABLE 11

Comparison of transformation results

| Recombinant strain | Danshensu Concentration g/L | Configuration | e.e % |
|---|---|---|---|
| E. coli HM (PG-gltS)/pCOLADuet-1-lfldhd-bsgdh-lct | 9.4 | R | >99.9 |
| E. coli HM (PG-gltS)/pCOLADuet-1-wcldhl-bsgdh-lct | 8.2 | S | >99.9 |
| E. coli HM/pCOLADuet-1-lfldhd-bsgdh-lct | 6.3 | R | >99.9 |
| E. coli HM/pCOLADuet-1-wcldhl-bsgdh-lct | 7.4 | S | >99.9 |

The E. coli HM (PG-gltS) with the best effect is named E. coli HMG.

Example 8

According to the method as in Example 7, a medium expression intensity constitutive promoter (PG) ahead of the E. coli glyceraldehyde-3-phosphate dehydrogenase gene (gpdA) is added ahead of the nadA and pdxJ genes in E. coli HMBY, and the sequence is shown in SEQ ID NO: 8. The plasmid is then introduced.

When expression of the gene nadA is enhanced, the E. coli HMBY genome is used as a template, nadA-FF/nadA-FR, nadA-gpdA-F/nadA-gpdA-R and nadA-RF/nadA-RR are used as primers, upstream sequences, promoters and downstream sequences are amplified, and nadA-FF and nadA-RR are used as primers to fuse an expression cassette containing the gpdA promoter. Then, after the expression cassette is transferred into E. coli HMBY together with plasmids pCasRed and pCRISPR-gDNA (containing nadA sgRNA), Cas9/sgRNA induces double-strand break at the nadA gene locus of the host, the recombinase Red integrates the gpdA promoter ahead of the nadA gene, and the gene is verified by sequencing.

When expression of the gene pdxJ is enhanced, the E. coli HMBY genome is used as a template, pdxJ-FF/pdxJ-FR, pdxJ-gpdA-F/pdxJ-gpdA-R and pdxJ-RF/pdxJ-RR are used as primers, upstream sequences, promoters and downstream sequences are amplified, and pdxJ-FF and pdxJ-RR are used as primers to fuse an expression cassette containing the gpdA promoter. Then, after the expression cassette is transferred into E. coli HMBY together with plasmids pCasRed and pCRISPR-gDNA (containing pdxJ sgRNA), Cas9/sgRNA induces double-strand break at the pdxJ gene locus of the host, the recombinase Red integrates the gpdA promoter ahead of the pdxJ gene, and the gene is verified by sequencing.

Table 12 below shows the corresponding indexes of the primer name and the sequence identity number.

TABLE 12

Primer name and sequence identity number

| Name | Sequence identity number |
|---|---|
| pdxJ sgRNA | SEQ ID NO: 13 |
| nadA sgRNA | SEQ ID NO: 1 |
| pdxJ-FF | SEQ ID NO: 14 |
| pdxJ-FR | SEQ ID NO: 15 |
| pdxJ-gpdA-F | SEQ ID NO: 16 |
| pdxJ-gpdA-R | SEQ ID NO: 17 |
| pdxJ-RF | SEQ ID NO: 18 |
| pdxJ-RR | SEQ ID NO: 19 |
| nadA-FF | SEQ ID NO: 2 |
| nadA-FR | SEQ ID NO: 3 |
| nadA-gpdA-F | SEQ ID NO: 4 |
| nadA-gpdA-R | SEQ ID NO: 5 |
| nadA-RF | SEQ ID NO: 6 |
| nadA-RR | SEQ ID NO: 7 |

After genetic modification is completed, the co-expression plasmid is introduced. According to the induction expression method described in Example 2, various types of cells are collected for transformation and analysis, and the results are shown in Table 13. In the whole cell transformation system with cell wet weight of 20 g/L, pyruvic acid of 100 g/L, levodopa of 120 g/L, glucose of 200 g/L, pH of 9.0, temperature of 30° C., and shaker speed of 250 rpm, the transformation time is 24 hours.

TABLE 13

Comparison of transformation results

| Strain | Danshensu Concentration g/L | Configuration | e.e % | Pyruvic acid g/L |
|---|---|---|---|---|
| E. coli HMBY (PG-pdxJ, PG-nadA)/pCOLADuet-1-lfldhd-ect1-bsgdh | 91.1 | R | >99.9 | 51.3 |
| E. coli HMBY (PG-pdxJ, PG-nadA)/pCOLADuet-1-wcldhl-ect1-bsgdh | 93.0 | S | >99.9 | 49.5 |
| E. coli HML (PG-pdxJ)/pCOLADuet-1-lfldhd-ect1-bsgdh | 73.1 | R | >99.9 | 42.7 |
| E. coli HMBY (PG-nadA)/pCOLADuet-1-lfldhd-ect1-bsgdh | 82.2 | R | >99.9 | 41.6 |

TABLE 13-continued

Comparison of transformation results

| Strain | Danshensu | | | Pyruvic acid g/L |
|---|---|---|---|---|
| | Concentration g/L | Configuration | e.e % | |
| E. coli HMBY/pCOLADuet-1-lfldhd-ect1-bsgdh | 65.4 | R | >99.9 | 34.6 |
| E. coli HMBY/pCOLADuet-1-wcldhl-ect1-bsgdh | 68.6 | S | >99.9 | 35.1 |

The *E. coli* HMBY(PG-nadA, PG-pdxJ) with the best effect is named *E. coli* NP.

After genetic modification is completed, the co-expression plasmid is introduced. According to the induction expression method as described in Example 2, various types of cells are collected for transformation and analysis, and the results are shown in Table 14. In the whole cell transformation system with wet cell weight of 20 g/L, L-lactic acid of 100 g/L, levodopa of 120 g/L, pH of 9.0, temperature of 30° C., and shaker speed of 250 rpm, the transformation time is 24 hours.

TABLE 14

Comparison of transformation results

| Strain | Danshensu | | | Alanine g/L |
|---|---|---|---|---|
| | Concentration g/L | Configuration | e.e % | |
| E. coli HML (PG-pdxJ, PG-nadA)/pCOLADuet-1-lfldhd-ect1-llldh | 89.5 | R | >99.9 | 44.9 |
| E. coli HML (PG-pdxJ, PG-nadA)/pCOLADuet-1-wcldhl-ect1-llldh | 91.8 | S | >99.9 | 48.8 |
| E. coli HML (PG-pdxJ)/pCOLADuet-1-lfldhd-ect1-llldh | 72.7 | R | >99.9 | 39.1 |
| E. coli HML(PG-nadA)/pCOLADuet-1-lfldhd-ect1-llldh | 80.4 | R | >99.9 | 40.3 |
| E. coli HML/pCOLADuet-1-lfldhd-ect1-llldh | 63.1 | R | >99.9 | 32.2 |
| E. coli HML/pCOLADuet-1-wcldhl-ect1-llldh | 66.2 | S | >99.9 | 33.9 |

The best-performing *E. coli* HML(PG-nadA,PG-pdxJ) is named *E. coli* NL.

After genetic modification is completed, the co-expression plasmid is introduced. According to the induction expression method described in Example 2, various types of cells are collected for transformation and analysis, and the results are shown in Table 15. In the whole cell transformation system with wet cell weight of 20 g/L, L-glutamic acid of 200 g/L, levodopa of 20 g/L, pH of 9.0, temperature of 30° C., and shaker speed of 250 rpm, the transformation time is 24 hours.

The best-performing *E. coli* HMG (PG-nadA, PG-pdxJ) is named *E. coli* HNP.

Example 9

According to the induction expression method as described in Example 2, cells are collected after induction expression of *E. coli* NP/pCOLADuet-1-lfldhd-ect1-bsgdh is completed, and in a 100 ml reaction system with the wet cell weight of 1 g/L, pyruvic acid of 1 g/L, levodopa of 1 g/L, glucose of 1 g/L, pH of 6.0, temperature of 15° C. and shaker speed of 250 rpm, the transformation time is 1 hour. As a result of measurement, the concentration of R-danshensu is 77 mg/L, and e.e %>99.9.

According to the induction expression method as described in Example 2, cells are collected after induction expression of *E. coli* NL/pCOLADuet-1-lfldhd-ect1-llldh is completed, and in a 100 ml reaction system with wet cell weight of 1 g/L, L-lactic acid of 1 g/L, levodopa of 1 g/L, pH of 6.0, temperature of 15° C. and shaker speed of 250 rpm, the transformation time is 1 hour. As a result of

TABLE 15

Comparison of transformation results

| Strain | Danshensu g/L | | |
|---|---|---|---|
| | Concentration g/L | Configuration | e.e % |
| E. coli HMG(PG-pdxJ, PG-nadA)/pCOLADuet-1-lfldhd-bsgdh-lct | 92.9 | R | >99.9 |
| E. coli HMG(PG-pdxJ, PG-nadA)/pCOLADuet-1-wcldhl-bsgdh-lct | 96.2 | S | >99.9 |
| E. coli HMG(PG-pdxJ)/pCOLADuet-1-efmdhd-bsgdh-lct | 73.4 | R | >99.9 |
| E. coli HMG(PG-nadA)/pCOLADuet-1-lfldhd-bsgdh-lct | 83.2 | R | >99.9 |
| E. coli HMG/pCOLADuet-1-lfldhd-bsgdh-lct | 67.0 | R | >99.9 |
| E. coli HMG/pCOLADuet-1-lfldhl-bsgdh-lct | 69.6 | S | >99.9 | measurement, the concentration of R-danshensu is 77 mg/L, and e.e %>99.9.

According to the induction expression method as described in Example 2, cells are collected after induction expression of E. coli HNP/pCOLADuet-1-efmdhd-bsgdh-lct is completed, and in a 100 ml reaction system with wet cell weight of 1 g/L, L-glutamic acid of 1 g/L, levodopa of 1 g/L, pH of 6.0, temperature of 15° C. and shaker speed of 250 rpm, the transformation time is 1 hour. As a result of measurement, the concentration of S-danshensu is 93 mg/L, and e.e %>99.9.

Example 10

According to the induction expression method as described in Example 2, cells are collected after induction expression of the strains in Table 16 is completed, and in a 100 ml reaction system with the wet cell weight of 200 g/L, pyruvic acid of 200 g/L, levodopa of 200 g/L, glucose of 200 g/L, pH of 8.5, temperature of 40° C. and shaker speed of 250 rpm, the transformation time is 48 hours. The results are measured after the precipitate is completely diluted and dissolved.

TABLE 16

Comparison of transformation results

| Strain | Danshensu | | | Alanine g/L |
|---|---|---|---|---|
| | Yield g/L | Configuration | e.e % | |
| E. coli NP/pCOLADuet-1-lfldhd-ect1-bsgdh | 182 | R | >99.9 | 91 |
| E. coli NP/pCOLADuet-1-wcldhl-ect1-bsgdh | 179 | S | >99.9 | 97 |
| E. coli NP/pCOLADuet-1-lfldhd-ect1-pmaao | 142 | R | >99.9 | 80 |
| E. coli NP/pCOLADuet-1-lfldhd-ect1-praao | 176 | R | >99.9 | 95 |
| E. coli NP/pCOLADuet-1-wcldhl-ect1-mmaao | 154 | S | >99.9 | 80 |
| E. coli NP/pCOLADuet-1-wcldhl-ect1-praao | 162 | 5 | >99.9 | 88 |

According to the induction expression method as described in Example 2, cells are collected after induction expression of the strains in Table 17 is completed, and in a 100 ml reaction system with wet cell weight of 200 g/L, L-lactic acid of 200 g/L, levodopa of 200 g/L, pH of 8.5, temperature of 40° C. and shaker speed of 250 rpm, the transformation time is 48 hours. The results are measured after the precipitate is completely diluted and dissolved.

TABLE 17

Comparison of transformation results

| Strain | Danshensu | | | Alanine g/L |
|---|---|---|---|---|
| | Concentration g/L | Configuration | e.e % | |
| E. coli NL/pCOLADuet-1-lfldhd-ect1-llldh | 180 | R | >99.9 | 87 |
| E. coli NL/pCOLADuet-1-wcldhl-ect1-llldh | 179 | S | >99.9 | 86 |
| E. coli NL/pCOLADuet-1-lfldhd-ect1-pmaao | 130 | R | >99.9 | 64 |
| E. coli NL/pCOLADuet-1-lfldhd-ect1-praao | 153 | R | >99.9 | 75 |
| E. coli NL/pCOLADuet-1-wcldhl-ect1-mmaao | 139 | S | >99.9 | 67 |
| E. coli NL/pCOLADuet-1-wcldhl-ect1-praao | 142 | S | >99.9 | 61 |

According to the induction expression method as described in Example 1, cells are collected after induction expression of the strains in Table 18 is completed, and in a 100 ml reaction system with wet cell weight of 200 g/L, L-glutamic acid of 20 g/L, levodopa of 200 g/L, pH of 8.5, temperature of 40° C. and shaker speed of 250 rpm, the transformation time is 48 hours. The results are measured after the precipitate is completely diluted and dissolved.

TABLE 18

Comparison of transformation results

| Strain | Danshensu | | |
|---|---|---|---|
| | Yield g/L | Configuration | e.e % |
| E. coli HNP/pCOLADuet-1-lfldhd-bsgdh-lct | 184.6 | R | >99.9 |
| E. coli HNP/pCOLADuet-1-wcldhl-bsgdh-lct | 186.2 | S | >99.9 |
| E. coli NPP/pCOLADuet-1-lfldhd-bsgdh-ect1 | 131.2 | R | >99.9 |
| E. coli HNP/pCOLADuet-1-lfldhd-rsgdh-ect2 | 161.9 | R | >99.9 |
| E. coli HNP/pCOLADuet-1-wcldhl-csgdh-lpt | 140.7 | S | >99.9 |

The above-mentioned enzymes and modification and construction of the co-expression genetic engineering strains thereof, the culture medium composition and culture method of the bacterial cells, and the whole cell biotransformation are only preferred examples of the present disclosure, and are not intended to limit the present disclosure. In theory, other bacteria, filamentous fungi, actinomycetes and animal cells can be genome-modified and used for multi-gene co-expression whole-cell catalysis. Any modifications and equivalent replacements made within the principles and spirit of the present disclosure fall within the scope of the present disclosure.

What is claimed is:

1. A recombinant *Escherichia coli* (*E. coli*) bacterium, wherein the recombinant *E. coli* simultaneously expresses:
   (i) an α-hydroxycarboxylate dehydrogenase from *Lactobacillus plantarum*, *Enterococcus faecalis*, *Bacillus coagulans*, *Weissella confusa*, or *Lactobacillus fermentum*,
   (ii) an L-α-amino acid transaminase from *L. plantarum* or *Lactobacillus paracasei*, and
   (iii) a glucose dehydrogenase from *Bacillus subtilis* or an L-lactate dehydrogenase from *Lactococcus lactis*, or an L-glutamate dehydrogenase from *E. coli*, *Rhodobacter sphaeroides*, *Clostridium symbiosum*, or *Bacillus subtilis*, and
   wherein the recombinant *E. coli* comprises a gene knockout of the hpaD and/or mhpB genes.

2. The recombinant *E. coli* according to claim 1, wherein the recombinant *E. coli* further comprises one or more genes selected from the group consisting of: a pyruvic acid transporter gene, an L-lactic acid transporter gene, a glutamic acid transporter gene, an NAD synthesis gene, a pyridoxal phosphate synthesis gene, and a combination thereof; and
   wherein the pyruvic acid transporter gene, the L-lactic add transporter gene and the glutamic add transporter gene are not expressed simultaneously.

3. The recombinant *E. coli* according to claim 2, wherein the one or more genes are selected from the group consisting of: pyruvic add transport-related genes, lldP, gltS, nadA, pdxJ, and a combination thereof, and wherein the pyruvic add transport-related genes are selected from btsT and ybdD.

4. The recombinant *E. coli* according to claim 3, comprising a constitutive promoter before the one or more genes.

5. The recombinant *E. coli* according to claim 1, wherein said *E. coli* is a BL21 strain.

6. A method for producing Danshensu by using the recombinant *E. coli* according to claim 1, comprising: carrying out whole cell transformation production in a whole cell transformation production system.

7. The method according to claim 6, wherein in the whole cell transformation production system, wet cell weight is 1-200 g/L, and levodopa concentration is 1-200 g/L;
   wherein when the recombinant *E. coli* simultaneously expresses the a-hydroxycarboxylate dehydrogenase, the L-a-amino acid transaminase and the glucose dehydrogenase, in the whole cell transformation production system, pyruvic acid concentration is 1-200 g/L, and glucose concentration is 1-200 g/L; and
   the whole cell transformation production system has a pH of 6.0-9.0, and reacts at 15-40° C. for 1-48 hours.

8. The method according to claim 6, wherein in the whole cell transformation production system, wet cell weight is 1-200 g/L, and levodopa concentration is 1-200 g/L;
   wherein when the recombinant *E. coli* simultaneously expresses the a-hydroxycarboxylate dehydrogenase, the L-a-amino acid transaminase and the L-lactate dehydrogenase, the whole cell transformation production system further comprises L-lactic acid of 1-200 g/L; and the whole cell transformation production system has a pH of 6.0-9.0, and reacts at 15-40° C. for 1-48 hours.

9. The method according to claim 6, wherein in the whole cell transformation production system, wet cell weight is 1-200 g/L, and levodopa concentration is 1-200 g/L;

wherein when the recombinant *E. coli* simultaneously expresses the a-hydroxycarboxylate dehydrogenase, the L-a-amino acid transaminase and the L-glutamate dehydrogenase, the whole cell transformation production system further comprises L-glutamic acid of 1-200 g/L; and the whole cell transformation production system has a pH of 6.0-9.0, and reacts at 15-40° C. for 1-48 hours.

\* \* \* \* \*

SEQUENCE LISTING

<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
ttaacggcgt cggcttcggg                                              20

<210> SEQ ID NO 2
<211> LENGTH: 25
<212> TYPE: DNA
<213> ORGANISM: Artificial Sequence
<220> FEATURE:
<223> OTHER INFORMATION: Synthetic DNA

<400> SEQUENCE: 2
tcgaatcctg cacgacccac cacta                                        25

<210> SEQ ID NO 3
<211> LENGTH: 50
<212> TYPE: DNA
<213> ORGANISM: Artificial Sequence
<220> FEATURE:
<223> OTHER INFORMATION: Synthetic DNA

<400> SEQUENCE: 3
tcggccactc atcaacatga ttcatcgaca ttagcgtaat attcgctgtt             50

<210> SEQ ID NO 4
<211> LENGTH: 50
<212> TYPE: DNA
<213> ORGANISM: Artificial Sequence
<220> FEATURE:
<223> OTHER INFORMATION: Synthetic DNA

<400> SEQUENCE: 4
aacagcgaat attcgctaa tgtcgatgaa tcatgttgat gagtggccga              50

<210> SEQ ID NO 5
<211> LENGTH: 50
<212> TYPE: DNA
<213> ORGANISM: Artificial Sequence
<220> FEATURE:
<223> OTHER INFORMATION: Synthetic DNA

<400> SEQUENCE: 5
tgtctggatc aaacattacg ctcatggttt tctcctgtca ggaacgttcg             50

<210> SEQ ID NO 6
<211> LENGTH: 50
<212> TYPE: DNA
<213> ORGANISM: Artificial Sequence
<220> FEATURE:
<223> OTHER INFORMATION: Synthetic DNA

<400> SEQUENCE: 6
cgaacgttcc tgacaggaga aaaccatgag cgtaatgttt gatccagaca             50

<210> SEQ ID NO 7
<211> LENGTH: 25
<212> TYPE: DNA
<213> ORGANISM: Artificial Sequence

```
<220> FEATURE:
<223> OTHER INFORMATION: Synthetic DNA

<400> SEQUENCE: 7
catccacgga caatgcgcgc agctg                                            25

<210> SEQ ID NO 8
<211> LENGTH: 1100
<212> TYPE: DNA
<213> ORGANISM: Artificial Sequence
<220> FEATURE:
<223> OTHER INFORMATION: Synthetic DNA

<400> SEQUENCE: 8
atgaatcatg ttgatgagtg gccgatcgct acgtgggaag aaaccacgaa actccattgc      60
gcaatacgct gcgataacca gtaaaaagac cagccagtga atgctgattt gtaaccttga     120
atatttattt tccataacat ttcctgcttt aacataattt tccgttaaca taacgggctt     180
ttctcaaaat ttcattaaat attgttcacc cgttttcagg taatgactcc aacttattga     240
tagtgtttta tgttcagata atgcccgatg actttgtcat gcagctccac cgattttgag     300
aacgacagcg acttccgtcc cagccgtgcc aggtgctgcc tcagattcag gttatgccgc     360
tcaattcgct gcgtatatcg cttgctgatt acgtgcagct ttcccttcag gcgggattca     420
tacagcggcc agccatccgt catccatatc accacgtcaa agggtgacag caggctcata     480
agacgcccca gcgtcgccat agtgcgttca ccgaatacgt gcgcaacaac cgtcttccgg     540
agcctgtcat acgcgtaaaa cagccagcgc tggcgcgatt tagccccgac atagccccac     600
tgttcgtcca tttccgcgca gacgatgacg tcactgcccg gctgtatgcg cgaggttacc     660
gactgcggcc tgagtttttt aagtgacgta aaatcgtgtt gaggccaacg cccataatgc     720
gggcagttgc ccggcatcca acgccattca tggccatatc aatgattttc tggtgcgtac     780
cgggttgaga agcggtgtaa gtgaactgca gttgccatgt tttacggcag tgagagcaga     840
gatagcgctg atgtccggcg gtgcttttgc cgttacgcac caccccgtca gtagctgaac     900
aggagggaca gctgatagaa acagaagcca ctggagcacc tcaaaaacac catcatacac     960
taaatcagta agttggcagc atcaccccgt tttcagtacg ttacgtttca ctgtgagaat    1020
ggagattgcc catcccgcca tcctggtcta agcctggaaa ggatcaattt tcatccgaac    1080
gttcctgaca ggagaaaacc                                               1100

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
tatgcccgtc gatcgcgccc                                                  20

<210> SEQ ID NO 10
<211> LENGTH: 120
<212> TYPE: DNA
<213> ORGANISM: Artificial Sequence
<220> FEATURE:
<223> OTHER INFORMATION: Synthetic DNA

<400> SEQUENCE: 10
ccaagatcac gcacgtaccg tcgatgtatc tctctgaact gccagggaaa aaccacggtt      60
```

```
agatcagcaa gcgttgccgg gaaatgggcg tcgataccat tatcgttttc gacacccact    120
```

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11

```
tcatcgagta cctcttgcgc    20
```

<210> SEQ ID NO 12
<211> LENGTH: 120
<212> TYPE: DNA
<213> ORGANISM: Artificial Sequence
<220> FEATURE:
<223> OTHER INFORMATION: Synthetic DNA

<400> SEQUENCE: 12

```
tagcctgata tgcacgctta tcttcactgt ctttcccact cgccgctggt gggatatgtc    60
aatggcgtga ttgccagcgc ccgcgagcgt attgcggctt ctcccctga actggtggtg    120
```

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13

```
cgtcgcggtc agtaatgtga    20
```

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14

```
gcagaagaag atggtcattg gcaac    25
```

<210> SEQ ID NO 15
<211> LENGTH: 50
<212> TYPE: DNA
<213> ORGANISM: Artificial Sequence
<220> FEATURE:
<223> OTHER INFORMATION: Synthetic DNA

<400> SEQUENCE: 15

```
tcggccactc atcaacatga ttcattcgct taggcataaa ttgccggaac    50
```

<210> SEQ ID NO 16
<211> LENGTH: 50
<212> TYPE: DNA
<213> ORGANISM: Artificial Sequence
<220> FEATURE:
<223> OTHER INFORMATION: Synthetic DNA

<400> SEQUENCE: 16

```
gttccggcaa tttatgccta agcgaatgaa tcatgttgat gagtggccga    50
```

<210> SEQ ID NO 17
<211> LENGTH: 50

<212> TYPE: DNA
<213> ORGANISM: Artificial Sequence
<220> FEATURE:
<223> OTHER INFORMATION: Synthetic DNA

<400> SEQUENCE: 17
tgacgcctaa cagtaattca gccatggttt tctcctgtca ggaacgttcg    50

<210> SEQ ID NO 18
<211> LENGTH: 50
<212> TYPE: DNA
<213> ORGANISM: Artificial Sequence
<220> FEATURE:
<223> OTHER INFORMATION: Synthetic DNA

<400> SEQUENCE: 18
cgaacgttcc tgacaggaga aaaccatggc tgaattactg ttaggcgtca    50

<210> SEQ ID NO 19
<211> LENGTH: 25
<212> TYPE: DNA
<213> ORGANISM: Artificial Sequence
<220> FEATURE:
<223> OTHER INFORMATION: Synthetic DNA

<400> SEQUENCE: 19
tcacagcaaa acgcttcgcc agaaa    25

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
gcggtagttg cattacgtcg    20

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
cggaaaatat ttaggtcagg    20

<210> SEQ ID NO 22
<211> LENGTH: 25
<212> TYPE: DNA
<213> ORGANISM: Artificial Sequence
<220> FEATURE:
<223> OTHER INFORMATION: Synthetic DNA

<400> SEQUENCE: 22
gcaggaggtt aagatgcaat tagat    25

<210> SEQ ID NO 23
<211> LENGTH: 50
<212> TYPE: DNA
<213> ORGANISM: Artificial Sequence
<220> FEATURE:
<223> OTHER INFORMATION: Synthetic DNA

<400> SEQUENCE: 23
tcggccactc atcaacatga ttcatacctg taagccaaaa gacgacgagt        50

<210> SEQ ID NO 24
<211> LENGTH: 50
<212> TYPE: DNA
<213> ORGANISM: Artificial Sequence
<220> FEATURE:
<223> OTHER INFORMATION: Synthetic DNA

<400> SEQUENCE: 24
actcgtcgtc ttttggctta caggtatgaa tcatgttgat gagtggccga        50

<210> SEQ ID NO 25
<211> LENGTH: 50
<212> TYPE: DNA
<213> ORGANISM: Artificial Sequence
<220> FEATURE:
<223> OTHER INFORMATION: Synthetic DNA

<400> SEQUENCE: 25
gcttgaatag ttttttcgta tccatggttt tctcctgtca ggaacgttcg        50

<210> SEQ ID NO 26
<211> LENGTH: 50
<212> TYPE: DNA
<213> ORGANISM: Artificial Sequence
<220> FEATURE:
<223> OTHER INFORMATION: Synthetic DNA

<400> SEQUENCE: 26
cgaacgttcc tgacaggaga aaccatgga tacgaaaaaa ctattcaagc         50

<210> SEQ ID NO 27
<211> LENGTH: 25
<212> TYPE: DNA
<213> ORGANISM: Artificial Sequence
<220> FEATURE:
<223> OTHER INFORMATION: Synthetic DNA

<400> SEQUENCE: 27
gatacccagc gccaggccga cgata                                   25

<210> SEQ ID NO 28
<211> LENGTH: 25
<212> TYPE: DNA
<213> ORGANISM: Artificial Sequence
<220> FEATURE:
<223> OTHER INFORMATION: Synthetic DNA

<400> SEQUENCE: 28
ggtggggatg gcttacatcc tgcac                                   25

<210> SEQ ID NO 29
<211> LENGTH: 50
<212> TYPE: DNA
<213> ORGANISM: Artificial Sequence
<220> FEATURE:
<223> OTHER INFORMATION: Synthetic DNA

<400> SEQUENCE: 29
tcggccactc atcaacatga ttcatcggat gcggcgtgaa cgctttatcc        50

<210> SEQ ID NO 30
<211> LENGTH: 50
<212> TYPE: DNA
<213> ORGANISM: Artificial Sequence

```
<220> FEATURE:
<223> OTHER INFORMATION: Synthetic DNA

<400> SEQUENCE: 30
ggataaagcg ttcacgccgc atccgatgaa tcatgttgat gagtggccga              50

<210> SEQ ID NO 31
<211> LENGTH: 50
<212> TYPE: DNA
<213> ORGANISM: Artificial Sequence
<220> FEATURE:
<223> OTHER INFORMATION: Synthetic DNA

<400> SEQUENCE: 31
cggcttttgc cagtgaatca aacatggttt tctcctgtca ggaacgttcg              50

<210> SEQ ID NO 32
<211> LENGTH: 50
<212> TYPE: DNA
<213> ORGANISM: Artificial Sequence
<220> FEATURE:
<223> OTHER INFORMATION: Synthetic DNA

<400> SEQUENCE: 32
cgaacgttcc tgacaggaga aaaccatgtt tgattcactg gcaaaagccg              50

<210> SEQ ID NO 33
<211> LENGTH: 25
<212> TYPE: DNA
<213> ORGANISM: Artificial Sequence
<220> FEATURE:
<223> OTHER INFORMATION: Synthetic DNA

<400> SEQUENCE: 33
tataacgatg ccggacaggc gctgc                                         25
```